United States Patent [19]
Thomas

[11] Patent Number: 5,397,317
[45] Date of Patent: Mar. 14, 1995

[54] DISPOSABLE ABSORBENT ARTICLE CORE INTEGRITY SUPPORT

[75] Inventor: Dennis A. Thomas, Cincinnati, Ohio

[73] Assignee: Procter and Gamble Company, Cincinnati, Ohio

[21] Appl. No.: 149,410

[22] Filed: Dec. 16, 1993

[51] Int. Cl.⁶ .................. A61F 13/15; A61F 13/20
[52] U.S. Cl. .................... 604/382; 604/358; 604/366; 604/367; 604/370; 604/372; 604/384; 604/385.1; 604/391
[58] Field of Search ............. 604/358, 365–367, 604/369–370, 372, 378, 382, 384, 385.1, 391

[56] References Cited

U.S. PATENT DOCUMENTS

| | | |
|---|---|---|
| 3,768,480 | 10/1973 | Mesek et al. |
| 3,860,003 | 1/1975 | Buell |
| 3,881,489 | 5/1975 | Hartwell |
| 3,913,579 | 10/1975 | Srinivasan et al. |
| 3,913,580 | 10/1975 | Ginnocchio |
| 4,534,769 | 8/1985 | De Jonckheere et al. |
| 4,573,986 | 3/1986 | Minetola et al. |
| 4,850,989 | 7/1989 | Villez |
| 4,950,264 | 8/1990 | Osborn, III |
| 5,019,065 | 5/1991 | Scripps |
| 5,058,247 | 10/1991 | Thomas et al. |
| 5,116,563 | 5/1992 | Thomas et al. |
| 5,135,522 | 8/1992 | Fahrenkrug et al. |
| 5,180,534 | 1/1993 | Thomas |

*Primary Examiner*—Randall L. Green
*Assistant Examiner*—P. Zuttarelli
*Attorney, Agent, or Firm*—Laurence R. Letson; Larry L. Huston

[57] ABSTRACT

A technique to preserve absorbent core integrity in a disposable article is described.

Columns which protrude from the backing sheet of an absorbent disposable article or personal wear garment and which project into the fibrous mass of an absorbent core overlaid onto a liquid impervious backing sheet are disclosed. A top sheet which is pervious to liquids overlies the core of fibrous material encapsulating the absorbent core in cooperation with the backing sheet. The top sheet also may carry similar columns. These columns act to restrict the movement of the fibers in the absorbent core and, more particularly, to enhance and maintain the integrity of the absorbent core whenever wet and/or placed under stress. These columns serve to resist and to diminish any disintegration of the absorbent core.

20 Claims, 4 Drawing Sheets

DISPOSABLE ABSORBENT ARTICLE CORE INTEGRITY SUPPORT

FIELD OF THE INVENTION

This invention relates to disposable absorbent articles and, specifically, to a technique to maintain the integrity of the absorbent core of disposable absorbent articles which enables the absorbent core to maintain its integrity whenever moistened, wet, or stressed by rubbing or movement.

BACKGROUND OF THE INVENTION

In order to position, retain, or hold absorbent cores such as those in disposable absorbent articles the core has been adhered or glued in place. One method deposits an adhesive or glue-type material onto a backing sheet whereon the absorbent core is positioned and thereby fixed in a spacial relationship to the other portions of the absorbent article. As the absorbent core is positioned in contact with the adhesive, the fibers which are on the surface of the core and thereby in contact with the adhesive thus are permanently attached to the backing sheet or the layers and remain fixed relative thereto. However, since the core typically is formed of fluffed cellulose or other absorbent fibers and the individual fibers are not adhered to each other in any way, only those fibers contacted specifically by the adhesive and thus fixed in their position are confined against undesired movement if or whenever the article and core receive moisture. The remainder of the core is free to move or separate.

A significant problem with any absorbent article occurs because the fibers of the absorbent core tend to shift and pull apart and the absorbent core loses its integrity should the absorbent core become wet and/or forces are exerted against it. Forces typically come from the wearer or user of the article due to normal movement in activities such as walking, bending, sleeping or sitting.

With the loss of the integrity of this core, the capability of the absorbent core to absorb and hold fluids is significantly degraded.

The fibers tend to separate if wet and when engaged by forces; thus, gaps in the absorbent core may form and permit the accumulation of fluids in that region without adequate absorbency to accommodate the fluid quantity.

Even though absorbent cores heretofore have been enclosed within an envelope of material, typically pervious to liquids on at least one side, the absorbent core contained therein may and can lose its structural integrity when wet.

According to this invention, the integrity of the fiber absorbent core is maintained even when wet by limiting displacement of the fibers in this core. A plurality of columns inserted into the absorbent fiber core or pad limits or restricts the movement of the core. The columns restrict movement of the fibers engaged by the columns to a very short distance, that between adjacent columns. Thus the columns will not only resist movement and core separation but also act to maintain a fairly even distribution of fibers and, therefore, fairly uniform absorbency. The columns preferably are formed on a backing sheet of a material impervious to liquids. The columns also may be formed on a top sheet, the top sheet being positioned next to the user or wearer of the article. The top sheet column would be projecting away from the user or wearer.

The columns are preferably formed by a process known as gravure printing. The polymeric material used to form the columns is typically polyethylene for use on polyethylene sheets or polypropylene for use on polypropylene sheets. The polymeric material is heated to the glass transition temperature of the material, Tg, and transformed into a softened and semi-liquid mass which then is deposited into cells or apertures on a gravure printing drum. The drum is rotated into face-to-face engagement with the sheet upon which the columns are to be formed and the softened or semi-molten material is contacted with the supporting sheet. As the supporting sheet is thereafter separated from the gravure printing drum or plate, the softened material will tend to string or pull out into an elongated form prior to cooling below its glass transition temperature, Tg. As the material is pulled out or strung into a plurality of vertical prongs and subsequently hardens, the prongs then are cut with the hot wire. It is important that the hot wire be disposed at a position which allows stretching of the material to occur prior to the material being severed, thereby leaving a series of columns protruding from the support sheet. Prophetically, excess height of the columns could be trimmed away by means of mechanical cutters and trimmers or by means of a hot wire which extends transverse to the sheet, at a height to allow the desired column height.

The gravure printing roll is maintained in a substantially one-to-one velocity ratio with the backing sheet; and as the backing sheet is separated from the printing roll, the columns will be pulled substantially perpendicular to the backing sheet. Depending upon preference, the columns may be of any cross-sectional shapes such as circular, oval, round, rectangular or triangular. The base end of the column is deposited on and joined to the backing sheet, typically by fusing with the material of the backing sheet at the column/support sheet interface as the heat softens the backing sheet.

The distal end of the column also may be of various configurations. Typical configurations may include a bulbous end, a hooked end, or sheared to form a pile from the columns otherwise cut off at a desired height. All of the above type terminations of the distal end are suitable as are any other form or shape of the distal end which may be inserted into the fiber mass of the absorbent core.

The absorbent core itself typically is a fluffed mass of cellulose fibers but it should be understood that it may be made of shredded foam or any other absorbent material. The fluffed core typically is deposited onto the support layer and pressed onto the columns formed on the support layer. As the columns penetrate and protrude into the absorbent core, they tend to limit the movement of the fibers of the absorbent core in a plane substantially parallel to the support layer. Movement of the fibers in directions corresponding to the axis of the projection is restricted by the construction of the absorbent article. A top sheet of liquid pervious sheet material may be provided with columns in a manner similar to or identical to that generally described above with the columns faced towards and projected into the fibrous absorbent core.

The top and backing sheets of the article then may be joined to form an envelope containing the absorbent core; if desired, attachment or fastening means for holding the article on the wearer in a position intended for both efficiency and comfort may be provided.

Significant and advantageous benefits resulting from the invention include improved wet integrity and improved uniformity of absorbency.

This invention will be described in more detail with reference to examples which are illustrated in the accompanying drawings.

FIGS. 1 and 2 show perspective views of an absorbent garment which advantageously incorporates the subject invention.

FIGS. 3 and 4 detail sectional views of the absorbent articles, illustrated in FIGS. 1 and 2, taken along Lines 3—3 and 4—4, respectively.

FIGS. 7A thru 7D illustrate various forms of columns which may be advantageously incorporated into the absorbent disposal articles.

Figure 8:
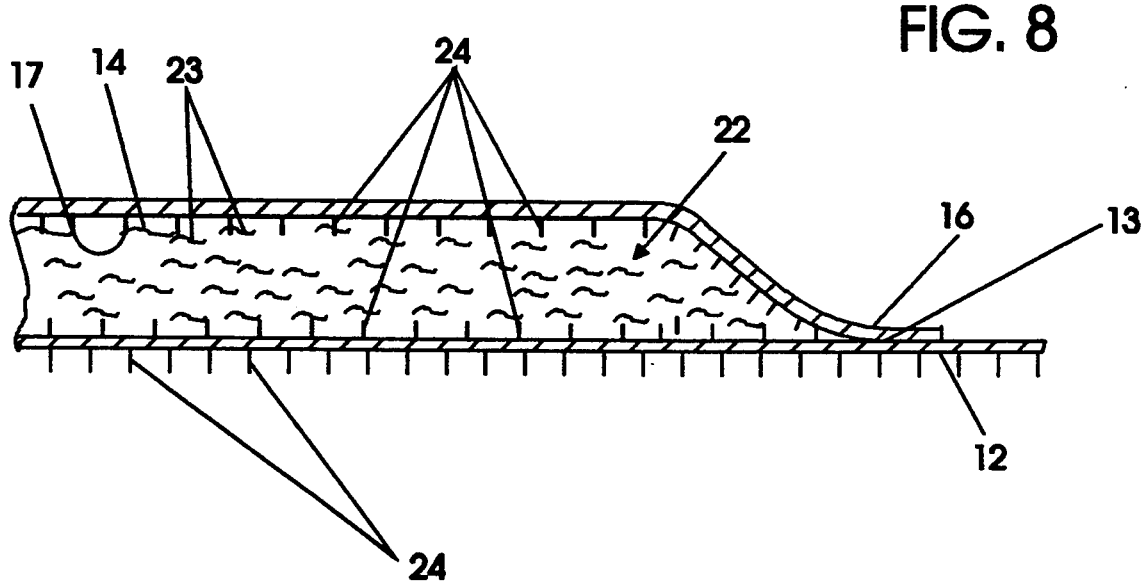

FIG. 8 is a sectional view of a bed pad with columns exposed on the backing sheet for engagement with bedding.

DETAILED DESCRIPTION OF THE INVENTION

The preferred embodiments of the invention are described below; referring initially to FIG. 1. A disposable diaper is illustrated. The diaper illustrated is of the type described in U.S. Pat. No. 3,860,003 issued to Kenneth Barclay Buell and commonly assigned herewith.

While a diaper is used for illustrative purposes, other disposable absorbent articles such as sanitary napkins or briefs can be fabricated using the invention described herein.

The foregoing U.S. Pat. No. 3,860,003 is incorporated herein by reference for the teaching of construction of a disposable absorbent article.

Figure 1:
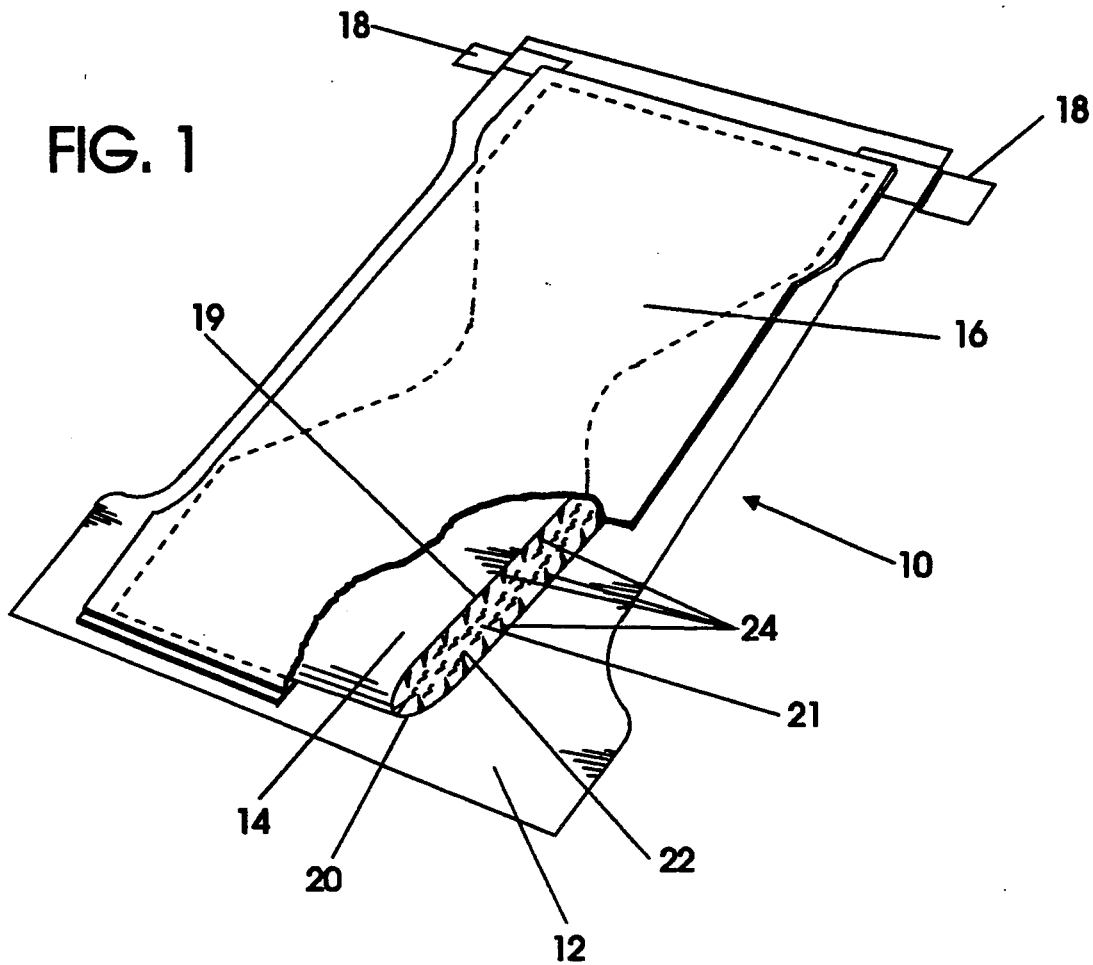

The disposable diaper of FIG. 1 is comprised of a backing sheet 12, absorbent core 14 and a top sheet 16. In addition, the disposable diaper 10 may further comprise attachment and retention tabs 18 to permit the attachment of the diaper 10 to the wearer as well as to retain it in the desired position relative to the wearer. The absorbent core 14 is preferably fabricated from a fluffed cellulose fiber pad 22 and may be contained within an envelope 19 formed of a liquid permeable sheet material 20. The liquid permeable sheet material 20 enveloping pad 22 may be manufactured of any material which is pervious to liquid, such as apertured film, woven or non-woven fabric. Formed onto one surface 21 of the enveloping material 20 are a plurality of columns 24 which project substantially perpendicular to the plane of the material forming the envelope 20. The columns 24 are physically attached or adhered to the surface 21 of the material 20 forming envelope 19 and project into the fibrous absorbent pad 22. The columns 24 do not significantly degrade the liquid pervious nature of material 20.

The absorbent core 14 is placed onto backing sheet 12 and then a top sheet 16 overlaid onto the backing sheet 12 and absorbent core 14. Top sheet 16 preferably is manufactured from materials which are hydrophobic, compliant, feel soft to touch, and nonirritating to the wearer's skin. A preferred top sheet could comprise polypropylene fibers having a denier of about 1.5, such as Hercules Type 151 polypropylene fibers marketed by Hercules, Incorporated of Wilmington, Del. Alternative materials for top sheets include porous foams, reticulated foams, apertured films, natural fibers (e.g., wood or cotton fibers), synthetic fibers (e.g., polyester or polypropylene fibers) or a combination of natural and synthetic fibers.

The top sheet 16 then is joined around its periphery to the backing sheet 12 by gluing, fusing or ultrasonic bonding. Other joining techniques may be used so long as the joint could not become a source of irritation to the wearer.

Figure 2:
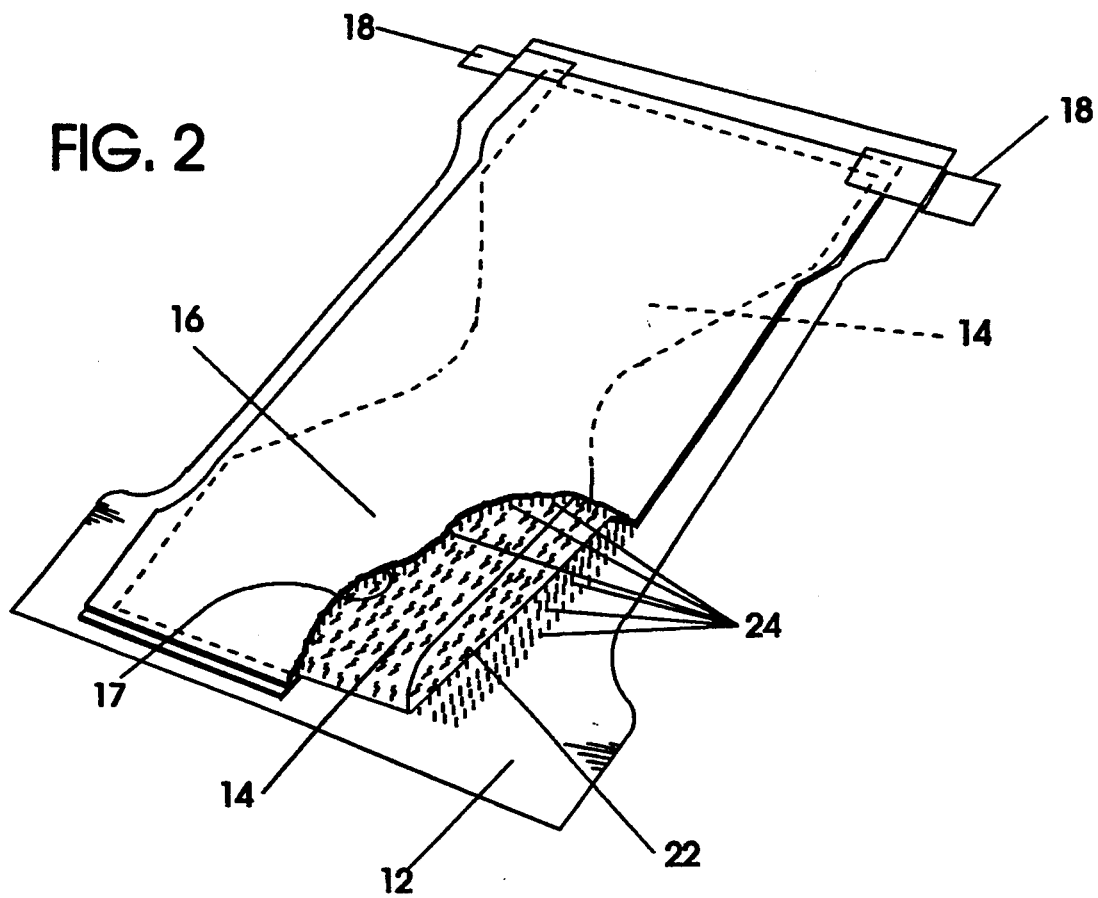

FIG. 2 illustrates an alternative embodiment where the columns 24 are formed directly on backing sheet 12 in a pattern which generally would correspond to the shape of the absorbent pad 22. The pattern may be controlled by the gravure printing drum or plate to be described below. The absorbent pad 22 forming the absorbent core 14 typically is a fluffed mass of absorbent fibers, such as cellulose, which may be directly deposited onto the backing sheet 12 and columns 24. Thereafter, a top sheet 16 is overlaid onto the backing sheet 12 and the absorbent core 14. The face 17 of top sheet 16 which engages absorbent core 14 is similarly provided with columns 24 substantially identical to the columns 24 formed on backing sheet 12. The top sheet 16 and backing sheet 12 then are joined or fused at the margins 13 to envelop and contain core 14. The significant difference between the embodiments illustrated in FIG. 2 and FIG. 1 is the elimination of the separate envelope 19 in FIG. 2.

Figure 3:
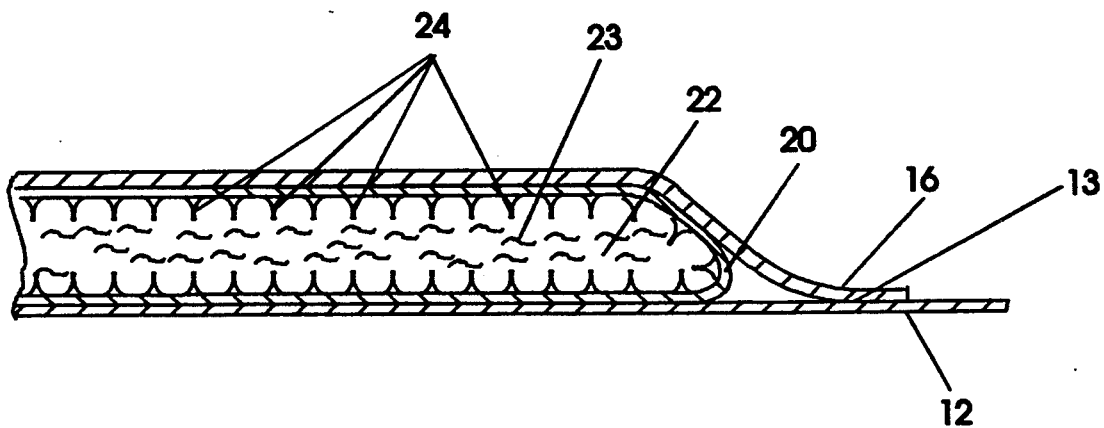

FIG. 3 is a partial sectional view of a disposable absorbent article such as a disposable diaper, disposable incontinence pad, sanitary napkins, panty liners or an absorbent bedding pad. The absorbent pad 22 is surrounded and contained by an envelope 19 having columns 24 extending from said envelope 19 into the pad 22 of fibers 23 thereon forming the absorbent core 14. The top sheet 16 and backing sheet 12 are illustrated as joined at periphery 13 by any desired and conventional technique, such as glue, heat fusing or ultrasonic bonding.

Figure 4:
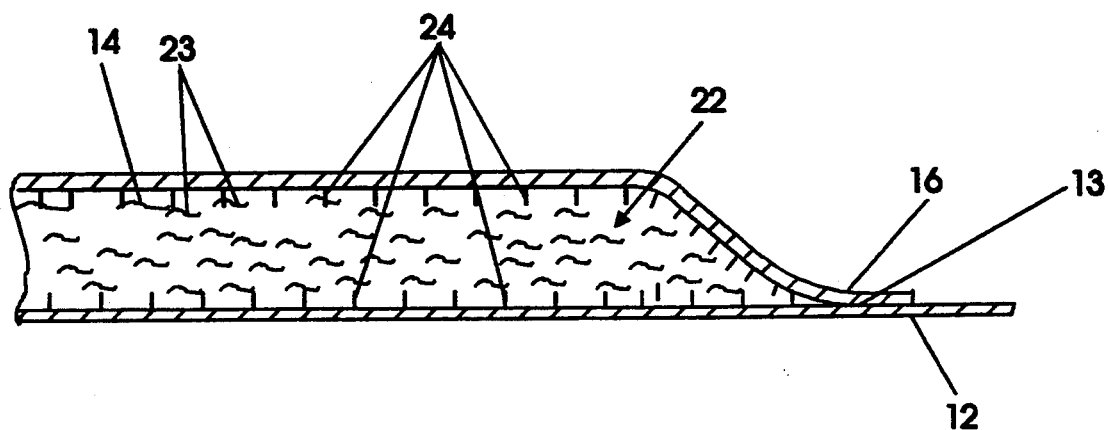

FIG. 4 illustrates a sectional view of a portion of an absorbent disposable personal article as in FIG. 3, wherein the top sheet 16 and backing sheet 12 each are provided with a plurality of columns 24 protruding from the surfaces of each of the sheets 16, 12, respectively, that project into the pad 22 of fibers 23 and that engage the fibers 23 which constitute at least a portion of the absorbent core 14. The absorbent core 14 in this embodiment does not have an envelope. Similar to the construction illustrated in FIG. 3, the margins of top sheet 16 and backing sheet 12 are joined or fused at a periphery 13.

The columns 24 which project from surfaces of top sheet 16 and backing sheet 12 preferably are formed by a gravure printing process. In the gravure printing process diagrammatically illustrated at FIG. 5, a backing roll 40 is provided to support sheet 42. Sheet 42 ultimately may become a backing sheet 12, top sheet 16 or envelope material 20 depending upon the type of sheeting selected and printed. One surface 41 of sheet 42 is engaged with gravure roller 44 which forms a nip 46 in cooperation with backing roll 40.

A reservoir 48 contains a quantity of materials, such as polyethylene or polypropylene dependent upon the material forming sheet 42, and is provided to supply the material contained in reservoir 48 to the cells or apertures 50 formed in the surface of gravure roller 44. A doctor blade 52 acts to prevent excessive quantities of the material within reservoir 48 from adhering to the surface 51 of gravure roller 44 at locations other than in cells or apertures 50. Backing roll 40 and gravure roller 44 rotate in the directions indicated by arrows 54 and 56, respectively, thereby transporting sheet 42 through the nip 46 and create continuous contact of a new portion of the surface of sheet 42 with the material from reservoir 48. The material, polyethylene or polypropylene or other suitable material, is heated to its glass transition temperature, Tg, and slightly above to transform the solid material into a thick semi-molten mass. As the heated material in the gravure cells or apertures 50 is contacted onto a face 41 of sheet 42, the heat contained therein will soften a minute region of the surface 41 of sheet 42, and the material contained in the gravure cells or apertures 50 will join to and be adhered or fused to sheet 42. As the gravure roller 44 is separated from sheet 42, the molten material from cells or apertures 50 will be pulled to form strings 25; upon cooling sufficiently below the glass transition temperature, Tg, of the material, strings 25 will be cut leaving a pile of columns 24 which project generally normal to the surface of sheet 42.

The columns 24 may project at an angle relative to sheet 42, but preferably have a component normal to the sheet 42. The columns 24 then may be trimmed by any suitable trimming device or technique, but the preferred approach is to use a hot wire 58 extended transverse to the direction of the movement of sheet 42 and displaced from the surface of sheet 42 by a distance to yield a plurality of columns 24 of substantially uniform height. The columns 24 then will be a form of stubble extending normally from the sheet 42.

The density of the columns 24 per square unit of measure will be a function of the number of gravure cells or apertures 50 formed into the printing surface 51 of printing drum 44. Alternatively, a screen, not shown, may be used and attached to the drum 44 to provide the gravure cells or apertures 50. Typical densities may range from as low as 144 columns per square inch to as high as 1600 columns per square inch, with a preferred density of approximately 400 to 600 columns per square inch. The apparatus described in FIG. 5 and its operation is substantially the same apparatus disclosed and described in U.S. Pat. No. 5,180,534 issued to Dennis A. Thomas, et al., and commonly assigned herewith and incorporated herein by reference.

The substantial difference in the two apparatuses is that the velocity ratio of the printing surface 51 of gravure roller 44 and the sheet 42 is maintained at a 1:1 ratio. This ratio tends to form the columns 24 in a substantially perpendicular orientation to the sheet 42. The process of U.S. Pat. No. 5,180,534 is modified such that the velocity ratio between the periphery of the gravure roller 44 and the sheet 42 is maintained at a 1:1 ratio, rather than the velocity differential disclosed in U.S. Pat. No. 5,180,534.

Figure 5:
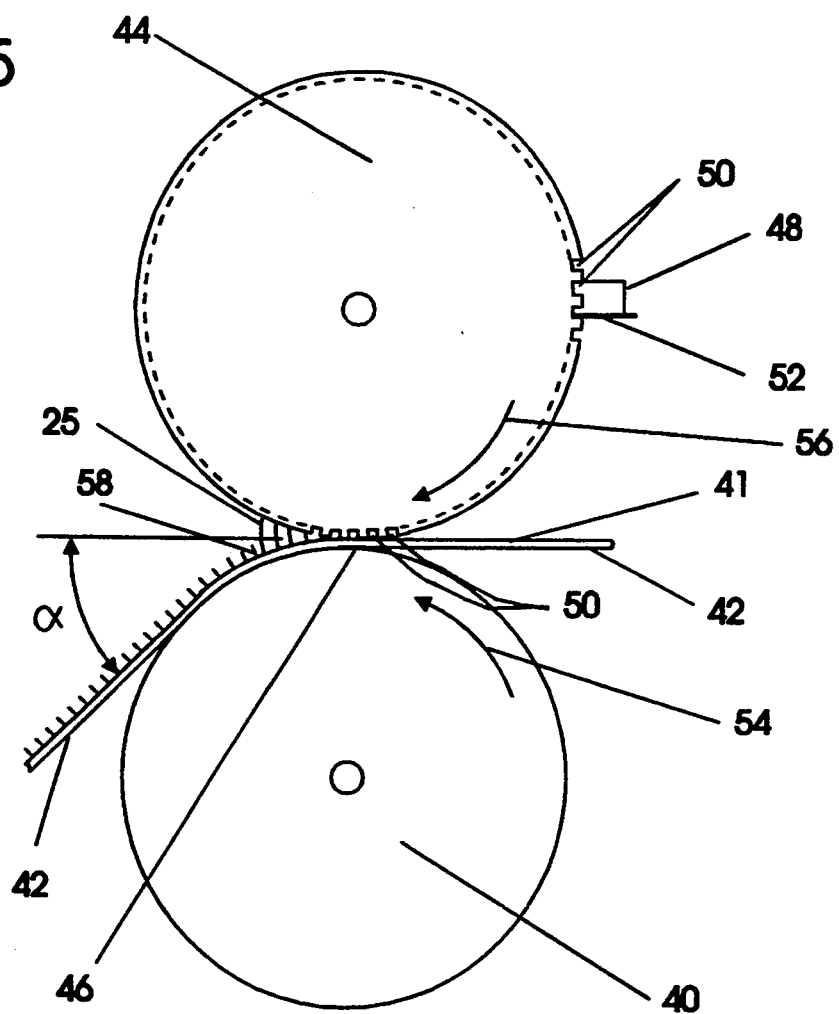
FIG. 5 illustrates a device for forming columns on sheet material.
Figure 6:
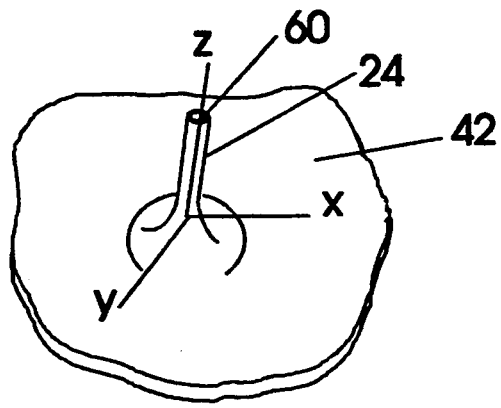
FIG. 6 is a typical column as well as a three axis reference diagram.

Referring now to FIG. 6, a typical column 24 is illustrated along with a segment of sheet 42 and additionally illustrates the terminal or distal end 60 of column 24. The distal end 60 in this illustration may result either from a clipping or shearing action or the use of the hot wire trimmer 58 as illustrated in FIG. 5. It is very possible, depending upon the temperature of the hot wire 58 and its relative location to the nip 46, that other forms of the tip 60 also may result from hot wire trimming.

As can be readily observed, with columns 24 extending upwardly from the sheet 42 if a fibrous absorbent core 24 is placed onto column 24 in a downward Z direction of movement, the column 24 will restrict the movement of the fibers 23 closely positioned to the column 24 and thus prevent movement in the XY plane. With movement constrained in the XY plane and additionally with a large number of similar columns 24 engaging the same or other fibers in the core 22, at least those fibers 23 near the surface of the core 22 become partially immobilized with the exception of movement in the Z direction.

Movement of fibers 23 in the Z direction is constrained by the fibrous absorbent core 22 being entrapped between a top sheet 16 and a backing sheet 12, as illustrated in any of FIGS. 1 thru 4.

The manufacture of the columns 24 may result in many different shapes, not only of the columns 24 but also of the tips 60 of the columns 24. Referring now to FIGS. 7A thru 7D, several different possible shapes of the columns 24A, 24B, 24C, and 24D are illustrated. The columns 24A thru 24D will be essentially free-formed during the manufacturing process. By the term free-form, it is intended to convey that there is no effort to make the columns 24A thru 24D conform to any precise shape or aspect ratio, but result from stringing the molten polymeric material after the molten polymeric material has contacted the sheet 42, which may subsequently be formed into top sheet 16, backing sheet 12, or material 20 of envelope 19, as illustrated in FIGS. 1 thru 4. It should be noted that the axis of the columns 24a thru 24d form an angle theta with respect to sheet 42. Angle theta is preferably 90 degrees but may vary acceptably therefrom to a limited amount. The angle is measured using the technique described in U.S. Pat. No. 5,180,534, and may satisfactorily deviate from the ideal 90 degrees by about 45 degrees resulting in an angle theta from 45 degrees to 90 degrees.

Figure 7A:
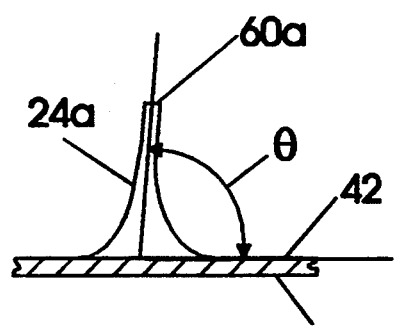

FIG. 7A illustrates a clipped distal end 60a either formed by mechanical shearing or by hot wire trimming, as previously described.

Figure 7B:
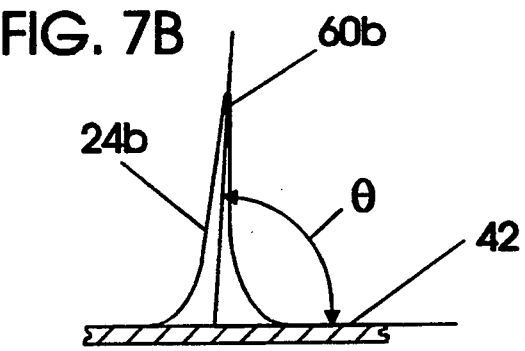

FIG. 7B illustrates a tip where the tip 60b as the natural result of the string 25 breaking during the manufacturing process.

Figure 7C:
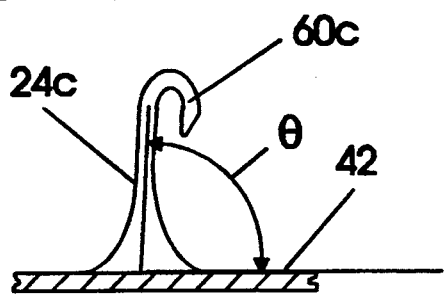

Tip 60c as shown in FIG. 7C illustrates a tip formed by the material drooping or collapsing from its own weight, a result either of slow cooling after the string 25 has broken or by a hot wire trimmer 58 severing the column 24, with the material being sufficiently hot to effectively delay the cooling of the material below its glass transition temperature, Tg, thus permitting the softened and molten material to fall over forming a hook as in tip 60c.

Figure 7D:
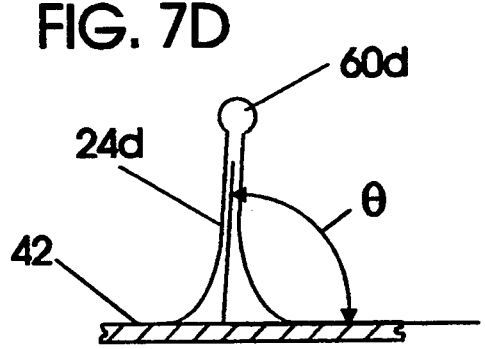

FIG. 7D illustrates a bulbous termination 60d of column 24d. This form may also be the result of a hot wire trimmer 58 whereby the material immediately adjacent to the hot wire 58 is sufficiently heated or reheated to flow and coalesce into a bulbous form on the top 60d of the otherwise rigid column 24d.

Inasmuch as any of these forms may be projected into the fibrous mass of the absorbent fiber core 14 and then restrict the movement of pad 22 in the XY plane, parallel to the surface of sheet 42, any of these terminations 60, 60a, 60b, 60c, 60d are acceptable.

The height of the completed columns 24 as shown in FIG. 6 for columns 24a thru 24d may be as much as 2½ to 3 millimeters, if the fiber absorbent core 14 is sufficiently thick or may be a fraction of a millimeter for a very thin core 14 with a preferred height of about one millimeter. The difference in the thickness in the cores 14 will depend to some extent upon the absorbency required for the particular article or the nature of the article. The use of the columns 24 to constrain movement and to preserve integrity of the absorbent core 14 may be advantageous not only in disposable diapers, but may also be used in catamenial products, bed pads and other absorbent articles wherein the integrity of the fiber absorbent core 14 must be maintained should the absorbent core 14 become wet, moist, or stressed.

An example of a catamenial product which may advantageously utilize the invention disclosed herein is disclosed and claimed in U.S. Pat. No. 4,950,264 issued to Thomas W. Osborn, III and commonly assigned herewith. This patent, U.S. Pat. No. 4,950,264 hereby is incorporated by reference herein for purposes of disclosure regarding the construction, fabrication and conformation of the disposal absorbent article disclosed therein. As with the disposable diaper 10 disclosed in FIGS. 1 or 2 of this specification, the absorbent pad 22 making up the absorbent core 14 may be made from any suitable absorbent material including wood pulp, creped cellulose wadding, absorbent foams, absorbent sponges, synthetic staple fibers, polymeric fibers, hydrogel forming polymer gelling agents, or any equivalent materials or combination of materials. The only requirement of the core 14 is that the columns 24 protruding from the sheet 42 as illustrated in FIG. 5 may be pressed into the core 14, regardless of whether the core 14 is contained such as by envelope 19 in FIG. 1 or is deposited as a loose batt or batting of material onto backing sheet 12 and overlaid by top sheet 16 as illustrated in FIG. 2.

For uses such as bed pads, it may be desirable to deposit the columns 24 onto both surfaces of a backing sheet 12 as shown in FIG. 8. The exposed columns 24 on the surface of backing sheet 12 will engage the bedding and resist slippage of the bed pad relative to the bedding. Nevertheless, a bed pad need not have columns 24 on the exposed surface of backing sheet 12.

It will be apparent to one skilled in the art that various other modifications and combinations of the columns 24, backing sheets 12, top sheets 16 and absorbent cores 14 may be fabricated into numerous different articles of an absorbent and disposable nature which may advantageously incorporate the integrity stabilization aspects of the present invention. Also, it will be apparent to one skilled in the art that minor modifications and changes may be made to different aspects of this invention and still fall within the scope of the appended claims.

What is claimed is:

1. A disposable absorbent product comprising:
   a backing sheet of a flexible sheet material, said backing sheet impervious to liquids and having a margin;
   a top sheet of a flexible sheet material, said cover sheet pervious to liquids and having a margin;
   said backing sheet and said top sheet separated by a mass of absorbent material;
   said backing sheet having disposed on a first surface thereof, said first surface being adjacent said absorbent material, a plurality of individual columnar stabilizing means for mechanically stabilizing said absorbent material, said columnar stabilizing means being joined to said backing sheet and inserted into said absorbent material;
   said top sheet and said backing sheet joined at said margins, thereby limiting movement of said absorbent material relative to said sheets.

2. The disposable absorbent product of claim 1 is a disposable diaper, wherein said diaper further comprises retaining means for retaining said product on and relative to a wearer.

3. The disposable absorbent product of claim 1 wherein each stabilizing means comprises a thermally sensitive material attached to said backing sheet and projecting from said backing sheet.

4. The disposable absorbent product of claim 3 wherein said stabilizing means project into and engages with said absorbent material.

5. The disposable absorbent product of claim 4 further comprising a further plurality of said columnar stabilizing means for stabilizing said backing sheet relative to fibrous material contacted with said product, formed onto and attached to a second surface of said backing sheet.

6. The disposable absorbent product of claim 3 wherein said stabilizing means comprises a distal end formed in a hook shape, whereby when engaged with said absorbent material, said hook shaped distal end will resist withdrawal from said absorbent material.

7. The disposable absorbent product of claim 4 wherein said stabilizing means comprises a distal end formed in a hook shape, whereby when engaged with said absorbent material, said hook shaped distal end will resist withdrawal from said absorbent material.

8. The disposable absorbent product of claim 6 wherein said columnar stabilizing means forms an included angle with said backing sheet of from about 45 degrees to 90 degrees.

9. The disposable absorbent product of claim 7 wherein said columnar stabilizing means forms an included angle with said backing sheet of from about 45 degrees to 90 degrees.

10. A disposable absorbent article for absorbing human fluid excretions, comprising:
    a liquid impervious sheet having at least two faces and margins;
    an absorbent batt disposed on one of said two faces of said sheet;
    a liquid pervious layer overlying said sheet and said absorbent batt, whereby said batt is intermediate said layer and said sheet;
    said sheet having a plurality of individual columns formed on at least one face of said sheet, wherein said columns penetrate into and mechanically stabilize said batt.

11. The disposable absorbent article of claim 10 further comprising said columns formed on two faces of said sheet, thereby forming a bed pad.

12. The disposable absorbent article of claim 10 wherein said absorbent batt is contained within an envelope of liquid pervious material, said envelope disposed between said liquid impervious sheet and said liquid pervious layer, said columns penetrating said envelope and said batt.

13. The disposable absorbent article of claim 12 further comprising said columns formed on two faces of said sheet, thereby forming a bed pad.

14. The disposable absorbent article of claim 10 further comprising a plurality of columns joined to and projecting from said liquid pervious layer into said batt.

15. The disposable absorbent article of claim 12 further comprising a plurality of columns joined to and projecting from said liquid pervious layer into said batt.

16. A method of maintaining integrity of and stabilizing an absorbent batt in a disposable absorbent article comprising the steps of:
   a. providing a first sheet of material with two faces;
   b. forming a plurality of individual columns on at least one of said faces on said sheet;
   c. depositing an absorbent batt onto said columns;
   d. inserting said columns into and mechanically stabilizing said absorbent batt;
   e. providing a liquid pervious sheet having two faces; and
   f. disposing said liquid pervious sheet overlying said first sheet and said absorbent batt.

17. The method of claim 16 including further steps of:
   forming a plurality of columnar projections on one of said faces of said liquid pervious sheet and disposing said liquid pervious sheet with said columns projecting toward said absorbent batt, and
   joining said liquid pervious sheet with said first sheet.

18. The method of claim 16 wherein said steps of forming a plurality of columns further comprises the steps of:
   1) providing a gravure printing surface having cells or apertures therein;
   2) filling said cells or apertures with a thermally sensitive material for transfer to a print receiving face of said first sheet;
   3) contacting and joining said thermally sensitive material with said print receiving face of said first sheet;
   4) separating said first sheet from said printing surface;
   5) stringing said thermally sensitive material to form a plurality of columns.

19. The method of claim 17 wherein said steps of forming a plurality of columns further comprises the steps of:
   1) providing a gravure printing surface having cells or apertures therein;
   2) filling said cells or apertures with a thermally sensitive material for transfer to a face of said first sheet and said liquid pervious sheet;
   3) contacting and joining said thermally sensitive material with said face of said liquid pervious sheet and said first sheet;
   4) separating said first sheet and said liquid pervious sheet from said printing surface;
   5) stringing said thermally sensitive material to form a pile of columns.

20. The method of claim 19 including the further steps of trimming said columns on said first and liquid pervious sheets to a substantially uniform height from each of said sheets.

* * * * *